(12) United States Patent
Dohlman et al.

(10) Patent No.: US 6,482,603 B1
(45) Date of Patent: Nov. 19, 2002

(54) METHOD OF DETECTING DRUG-RECEPTOR AND PROTEIN-PROTEIN INTERACTIONS

(75) Inventors: Henrik G. Dohlman, Branford, CT (US); Kathleen N. Ehrhard, Longmeadow, MA (US)

(73) Assignee: Yale University, New Haven, CT (US)

( * ) Notice: Subject to any disclaimer, the term of this patent is extended or adjusted under 35 U.S.C. 154(b) by 60 days.

(21) Appl. No.: 09/709,626

(22) Filed: Nov. 13, 2000

Related U.S. Application Data (62) Division of application No. 09/296,607, filed on Apr. 23, 1999, now Pat. No. 6,242,205.
(60) Provisional application No. 60/082,940, filed on Apr. 24, 1998.

(51) Int. Cl.[7] .................. G01N 33/53; G01N 33/569; C12N 1/18
(52) U.S. Cl. .................. 435/7.8; 435/7.1; 435/7.21; 435/7.31; 435/69.1; 435/254.2
(58) Field of Search .................. 435/7.1, 69.1, 435/254.2, 7.21, 7.31, 7.8

(56) References Cited

U.S. PATENT DOCUMENTS

| | | | |
|---|---|---|---|
| 5,482,835 A | 1/1996 | King et al. ..................... | 435/6 |
| 5,739,029 A | 4/1998 | King et al. ............ | 435/254.21 |
| 5,876,951 A | 3/1999 | Fowlkes et al. ......... | 435/257.3 |

OTHER PUBLICATIONS

Garcia et al., A Rat Brain SEC1 Homologue Related to Rop and UNC18 Interacts with Syntaxin, *Proceedings of the National Academy of Science USA*, 91:2003–2007 (1994).

Song et al., Regulation of Membrane and Subunit Interactions by N–Myristoylation of a G Protein α Subunit in Yeast, *Journal of Biological Chemistry*, 271:20273–20283 (1996).

Vidal et al., Genetic Characterization of a Mammalian Protein–Protein Interaction Domain by Using a Yeast Reverse Two–Hybrid System, *Proceedings of the National Academy of Science USA*, 93:10321–10326 (1996).

Price et al., Functional Coupling of a Mammalian Somatostatin Receptor to the Yeast Pheromone Response Pathway, *Molecular and Cellular Biology*, 15:6188–6195 (1995).

Mende et al., The G Protein γ Subunit, *Journal of Biological Chemistry*, 270:15892–15898 (1995).

*Primary Examiner*—Mary E. Mosher
(74) *Attorney, Agent, or Firm*—Morgan, Lewis & Bockius

(57) ABSTRACT

The present invention relates to methods for detecting interactions between two proteins as well as detecting the modulation of those interactions. The present invention is based upon the discovery of a new non-nuclear system utilizing G protein gamma subunit fusions to detect the interactions between two proteins and is particularly useful for the detection of the interaction between two or more proteins wherein one of the proteins is associated with the cell membrane. Related methods, compositions and kits can be used to detect or assay the interactions between essentially any two proteins that can be expressed in a cell.

15 Claims, 4 Drawing Sheets

FIG. 1A
TRADITIONAL 2-HYBRID METHOD
X-Y INTERACTION IN THE NUCLEUS DRIVES REPORTER GENE TRANSCRIPTION

FIG. 1B
NEW METHOD
X-Y INTERACTION AT THE MEMBRANE BLOCKS Gβ/γ-MEDIATED SIGNAL

SEQUENCE LISTING

```
<160> NUMBER OF SEQ ID NOS:  6

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence:  5' PCR
      primer for STE18 (G gamma gene)

<400> SEQUENCE: 1
gggaattcaa tggctcacca tcaccatcac catgctagca tgacatcagt tcaaaactct        60
cc                                                                      62

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:  3' PCR
      primer for STE18 (G gamma gene)

<400> SEQUENCE: 2
gaggctctac gtagcaag                                                     18

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:  5' cloning
      primer for GAL4-STE18 sequence

<400> SEQUENCE: 3
ccgaattcca tggccattgg cctcaag                                           27

<210> SEQ ID NO 4
<211> LENGTH: 38
<212> TYPE: DNA
```

-continued

```
<213> ORGANISM: Artificial Sequence
<220> FEATURE:
<223> OTHER INFORMATION: Description of Artificial Sequence:  3' cloning
      primer for GAL4-STE18 sequence

<400> SEQUENCE: 4
cctgaattcg agcttatttc ttcgtctgtt ttattcag                                 38

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:  5' PCR
      primer for rat syntaxin 1a gene

<400> SEQUENCE: 5
cgcgggtcga catgaaggac cgaacccagg                                          30

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:  3' PCR
      primer for rat syntaxin 1a gene

<400> SEQUENCE: 6
ccgaattcac tatccaaaga tgcccccgat gg                                       32
```

METHOD OF DETECTING DRUG-RECEPTOR AND PROTEIN-PROTEIN INTERACTIONS

CROSS-REFERENCE TO RELATED APPLICATIONS

This application is a divisional application of U.S. Appl. Ser. No. 09/296,607, filed Apr. 23, 1999, now U.S. Pat No. 6,242,205, and claims the benefit of U.S. Provisional Appl. No. 60/082,940, filed Apr. 24, 1998, which is herein incorporated by reference in its entirety.

ACKNOWLEDGMENT OF FEDERAL SUPPORT

The present invention arose in part from research funded by the following federal grant monies: GM 553160.

TECHNICAL FIELD

The present invention relates to methods for detecting interactions between two proteins as well as detecting the modulation of those interactions. The present invention is based upon the discovery of a new non-nuclear system to detect the interactions between two proteins and is particularly useful for the detection of the interaction between two or more proteins wherein one of the proteins is associated with the cell membrane. Related methods, compositions and kits can be used to detect or assay the interactions between essentially any two proteins that can be expressed in a cell.

BACKGROUND OF THE INVENTION

A fundamental area of inquiry in biology is the analysis of interactions between proteins. Proteins are complex macromolecules made up of covalently linked chains of amino acids. Each protein assumes a unique three dimensional shape determined principally by its sequence of amino acids. Many proteins consist of smaller units termed domains, which are continuous stretches of amino acids able to fold independently from the rest of the protein. Some of the important forms of proteins are enzymes, polypeptide hormones, receptors, nutrient transporters, structural components of the cell, hemoglobins, antibodies, nucleoproteins, and components of viruses.

Protein-protein interactions enable two or more proteins to associate. A large number of non-covalent bonds form between the proteins when two protein surfaces are precisely matched. These bonds account for the specificity of recognition. Protein-protein interactions are involved, for example, in the assembly of enzyme subunits; in antigen-antibody reactions; in forming the supramolecular structures of ribosomes, filaments, and viruses; in transport; and in the interaction of receptors on a cell with growth factors and hormones. Products of oncogenes can give rise to neoplastic transformation through protein-protein interactions. For example, some oncogenes encode protein kinases whose enzymatic activity on cellular target proteins leads to the cancerous state. Other examples of protein-protein interaction include when a virus infects a cell by recognizing a polypeptide receptor on the surface and when platelets aggregate during thrombosis.

Protein-protein interactions have been generally studied in the past using biochemical techniques such as cross-linking, co-immunoprecipitation and co-fractionation by chromatography. A disadvantage of these techniques is that interacting proteins often exist in very low abundance and are, therefore, difficult to detect. Another major disadvantage is that these biochemical techniques involve only the proteins, not the genes encoding them. When an interaction is detected using biochemical methods, the newly identified protein often must be painstakingly isolated and then sequenced to enable the gene encoding it to be obtained. Another disadvantage is that these methods do not immediately provide information about which domains of the interacting proteins are involved in the interaction.

To alleviate the problems associated with the biochemical characterization of protein-protein interactions, genetic systems have been invented that are capable of rapidly detecting which proteins interact with a known protein, determining which domains of the proteins interact, and providing the genes for the newly identified interacting proteins. One such system is the yeast two-hybrid system wherein two proteins are expressed in yeast: one protein of interest fused to a DNA-binding domain and the other protein of interest fused to a transcriptional activation domain (Fields et al. (1989) *Nature* 340:245; Gyuris et al. (1993) *Cell* 75:791; Harper et al. (1993) *Cell* 75:805; Serrano et al. (1993) *Nature* 366:704; and Hannon et al. (1993) *Genes & Dev.* 7:2378). If the proteins interact, they activate transcription of a reporter gene that contains a binding site for the DNA-binding protein.

Although the development of genetic systems that utilize direct activation of a reporter gene, such as the yeast two-hybrid systems, has greatly facilitated the study of protein-protein interactions, many problems remain to be solved. For instance, the yeast two-hybrid systems rely on interactions between the two proteins in the nucleus of the cell. Accordingly, yeast two-hybrid systems are not useful for the study of integral membrane protein interactions and cannot be used to test cell membrane impermeate drugs. Furthermore, the study of protein-protein interactions wherein one of the proteins is itself a transcriptional activator often results in the transcription of the reporter gene without interaction between the two proteins under study. Lastly, the yeast two-hybrid systems require that both proteins under study be expressed as fusion proteins resulting in the possible loss of function.

SUMMARY OF THE INVENTION

The present inventors have discovered a genetic system to study protein-protein interactions that solves many of the problems associated with existing genetic systems. This system utilizes the receptor-G protein signaling system present in yeast and other eukaryotic cells to study protein-protein interactions, including the interactions wherein one protein is an integral membrane protein.

The present invention includes kits, vectors and methods for detecting one or more interactions between two proteins, comprising the steps of providing a cell with a first protein fused to a G protein gamma subunit and a second protein; and determining whether the interaction of the G protein gamma subunit with an effector molecule has been modulated, thereby determining whether the first and second proteins interact.

The present invention also includes kits, vectors and methods to identify an agent that modulates at least one interaction between two proteins, comprising the steps of exposing a cell to the agent, the cell comprising a first protein fused to a G protein gamma subunit and a second protein; and determining whether the interaction of the G protein gamma subunit with an effector molecule has been modulated.

The present invention further provides kits, vectors and methods to identify binding partners of a protein, comprising the steps of transforming or transfecting host cells with a library comprising a population of nucleic acid molecules which express a first protein fused to a G protein gamma subunit to produce a host cell population, said population of nucleic acids differing with respect to the first protein fused to a G protein gamma subunit; transforming the host cell population with a vector which expresses a second protein; culturing said host cell under conditions which express said first and second protein; and determining the activity of an effector molecule which is capable of interacting with the G protein gamma subunit. dr

BRIEF DESCRIPTION OF THE DRAWINGS

FIGS. 1A–1B.

FIGS. 2A–2B.

FIGS. 3A–3B.

MODES OF CARRYING OUT THE INVENTION
GENERAL DESCRIPTION

General Description

The present invention utilizes the heterotrimeric G protein (guanine nucleotide binding regulatory protein) regulatory mechanisms found in all eukaryotic cells to study protein-protein interactions. When functioning normally, G proteins act as an integral part of the signal traduction mechanisms by which extracellular hormones and other extracellular signaling molecules convey their signals through the plasma membrane of the cell and thus elicit appropriate intracellular responses.

Heterotrimeric G proteins are composed of three polypeptide subunits, namely G alpha, G beta and G gamma. The conformation the alpha subunit and the degree of association between all three subunits changes during the signal transduction process. These changes are associated with the hydrolysis of the nucleotide GTP to form GDP and Pi. The binding sites for GTP and GDP as well as the GTPase catalytic site reside in the alpha subunit.

The G protein cycle which occurs each time a signal is conveyed across the membrane can be summarized as follows. In an unstimulated cell, the G proteins are found in the resting state in which alpha, beta and gamma are complexed together and GDP is bound to G alpha. The binding of an appropriate hormone or other signaling molecule to a G protein coupled receptor at the cell surface initiates a signaling event when the ligand-activated receptor stimulates the alpha subunit to exchange GDP for GTP. In the active form, the alpha subunit, bound to GTP, dissociates from the beta-gamma complex, and the subunits then interact specifically with cellular effector molecules to evoke a cellular response. G protein beta-gamma complexes, and in some instance alpha subunits, can interact with different effector systems (e.g., phospholipase C, adenylyl cyclase systems, etc.) to evoke a variety of cellular responses.

The present invention uses the ability of the dissociated beta-gamma complex to specifically interact with cellular effector molecules to evoke a cellular response as an endpoint in assays to detect protein-protein interactions. This ability of the beta-gamma complex to interact with cellular effector molecules generally requires that the beta-gamma complex be free of the alpha subunit. The present inventors have discovered that interactions between the beta-gamma complex dissociated from the alpha subunit and an effector molecule can be prevented or inhibited by the association of the beta-gamma complex with another unrelated protein.

Figure 1A:
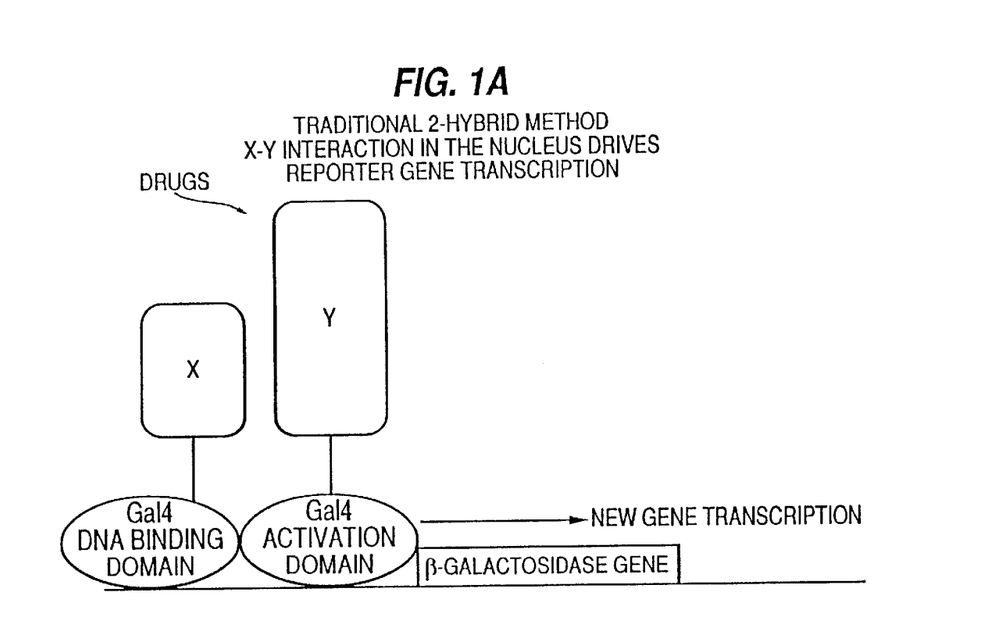
FIGS. 1A and 1B are schematics comparing the traditional yeast two-hybrid methods of detecting protein-protein interactions to the methods of the invention. Proteins X and Y of FIG. 1B correspond to the first and second proteins of the claimed methods, respectively.
Figure 1B:
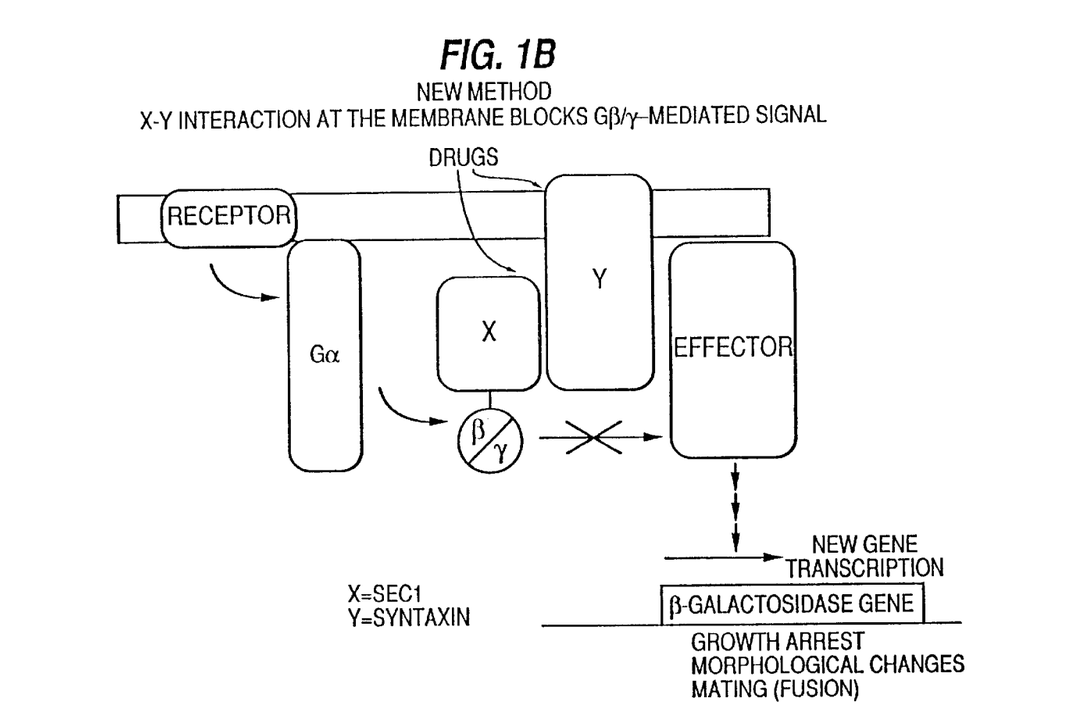

The methods of the invention comprise the expression of a first protein of interest fused in frame to a G protein gamma subunit. This G protein gamma subunit fusion is then expressed in the same cell as a second test protein which is typically expressed in native form. Interactions, such as binding, between the first protein fused to a G protein gamma subunit and the second test protein are assayed by determining whether the fused G protein gamma subunit in its association with the beta subunit is capable of interacting with effector molecules. In instances where the first protein fused to a G protein gamma subunit and the second protein interact or bind, the fused G protein gamma subunit in its association with the beta subunit is not free to interact with effector molecules. In contrast, when the first protein fused to a G protein gamma subunit and the second protein do not interact or bind, the fused G protein gamma subunit in its association with the beta subunit is free to interact with effector molecules (see FIG. 1).

Specific Embodiments

Definitions

As used herein, the term "agent" means any molecule that is randomly selected or rationally designed. As used herein, an agent is said to be randomly selected when the agent is chosen randomly without considering the specific sequences involved in the association of the proteins under study or the known functions of the proteins under study. Examples of randomly selected agents are chemical libraries, peptide combinatorial libraries, or a growth broth of an organism.

As used herein, an agent is said to be rationally selected or designed when the agent is chosen on a nonrandom basis which takes into account the sequence of the proteins under study and/or their conformation in connection with the agent's action. Agents can be rationally selected or rationally designed by utilizing the amino acid sequences that make up potential contact sites between the proteins. For example, a rationally selected peptide agent can be a peptide whose amino acid sequence is identical to an identified contact site on one of the proteins under study. Such an agent will reduce or block the association of the protein with its binding partner by binding to the contact site on the first protein.

The agents of the present invention can be, as examples, peptides, small molecules, nucleic acids, vitamin derivatives, as well as carbohydrates. A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents are antibodies immunoreactive with one of the proteins under study. Particularly useful are antibodies immunoreactive with the extracellular domain of membrane proteins under study. As described above, antibodies are obtained by immunization of suitable mammalian subjects with peptides, containing as antigenic regions, those portions of the protein intended to be targeted by the antibodies. Critical regions include the contact sites between the two proteins as well as extracellular regions of membrane proteins.

As used herein, the phrase "at least one interaction" refers to an interaction between the first protein fused to a G protein gamma subunit and the second protein detectable in the methods of the invention. Such interactions are typically, but not always, a form of direct interaction such as binding.

As used herein, the term "modulates" refers to any change in an interaction between the first protein fused to a G protein gamma subunit and the second protein, wherein that change is detectable by the methods of the invention. The term "modulates" includes inhibition or promotion of at least one interaction between a first protein fused to a G protein gamma subunit and the second protein.

As used herein, the term "cell" refers to any eukaryotic cell which contains a G protein coupled signaling system. Preferred cells include, but are not limited to, yeast cells such as *Saccharomyces cerevisiae* or *Schizosaccharomyces pombe* as well as insect, plant and mammalian cells in culture.

As used herein, the term "fused" refers to a protein which has been expressed from a recombinant gene which comprises the coding sequence from the first protein covalently attached in frame to a G protein gamma subunit gene. This recombinant gene when transcribed and translated produces a chimeric protein comprising the amino acid sequence of the first protein and the amino acid sequence of a G protein gamma subunit. Typically, the first gene is fused in frame to the coding sequence of a protein gamma subunit to produce a chimeric protein wherein the first protein is fused to the N or amino terminus of the G protein gamma subunit.

As used herein, the phrase "G protein gamma subunit" refers to any available G protein gamma subunit from a eukaryotic cell. G protein gamma subunits are known to be highly variable with over eleven gamma subunit genes isolated and various splice variants identified. See Hildebrand (1997) *Biochem. Pharm.* 54:325–339. The phrase also includes fragments of a G protein gamma subunit that retain the ability to interact with a G protein beta subunit and retain the ability to interact with at least one effector molecule. Preferably, G protein gamma subunits are selected from species corresponding to the selected host cell.

The term "first protein" refers to any protein employed in the methods of the invention to detect protein-protein interactions. The first test protein is fused to a G protein gamma subunit.

The term "second protein" refers to any protein employed in the methods of the invention to detect protein-protein interactions. The second test protein is not limited to any specific class of cellular proteins but specifically includes membrane proteins.

As used herein, the term "effector molecule" refers to any G protein gamma-beta target that results in an assayable phenotype upon interaction with a G protein gamma-beta complex. Many G protein effector molecules or targets have been identified including ion channels $I_{KG}$, and $I_{Ca}$, phospholipase $A_2$, STE20, STE5, PLCβ, adenylyl cyclases, G protein coupled receptor kinases, PI3K, the MAP kinase cascade, Bruton tyrosine kinase, Tsk tyrosine kinase, arrestins and phosphodiesterases. See Clapham et al. ((1997) *Ann. Rev. Pharmacol. Toxicol* 37:167–203) for a review of known effector molecules or targets.

As used herein, the term "membrane protein" refers to a protein that comprises at least one membrane spanning domain. Such membrane spanning domains typically comprise as series of hydrophobic amino acid residues that span the lipid bilayer membrane of a cell.

As used herein, the phrase "native form" refers to the expression of a protein without alteration of its primary amino acid sequence and/or secondary structure. For instance, a protein expressed in its native form is not expressed as a fusion protein.

As used herein, the term "sequestered" refers to any means of preventing the interaction of a gamma-beta complex which is dissociated from the alpha subunit with an effector molecule. The term includes, but is not limited to, the physical retention of the gamma-beta complex in or on the cell membrane by the interaction of the first and second proteins.

As used herein, the term "library" generally refers to either a collection of cDNA molecules corresponding to a population of mRNA isolated from a selected cell type, or the proteins encoded by the cDNA library. Methods to produce cDNA libraries from a selected cell population are commonly available, such as the methods disclosed by Sambrook et al. (Molecular Cloning, Cold Spring Harbor Laboratory Press, 1989). cDNA libraries from selected cell types are also commercially available from vendors such as Stratagene®.

As used herein, the term "detectable phenotype" refers to any phenotype which may be detected by physical, visual or chemical means elicited by the interaction of a beta-gamma complex with an effector molecule. Detectable phenotypes utilized in the invention include but are not limited to yeast pheromone induced growth inhibition, other forms of detectable cellular morphology changes as well as the activities of reporter genes such as lacZ and HIS3 operably linked to pheromone responsive promoters such as the BAR1 or FUS1 promoters (see U.S. Pat. No. 5,482,835).

Methods for Detecting protein-Protein Interactions

In one embodiment, the present invention makes use of a gene hybrid that encodes a first protein fused to a G protein gamma subunit. Interactions, such as binding, between the first protein fused to a G protein gamma subunit and the second test protein is assayed by determining whether the fused G protein gamma subunit in its association with the beta subunit is capable of interacting with effector molecules upon induction of a G protein signaling cascade. In instances where the first protein fused to a G protein gamma subunit and the second test protein interact or bind, the fused G protein gamma subunit in its association with the beta subunit is not free to interact with effector molecules. In contrast, when the first protein fused to a G protein gamma subunit and the second protein do not interact or bind, the fused G protein gamma subunit in its association with the beta subunit is free to interact with effector molecules (see FIG. 1).

The methods of the invention include providing a host cell, preferably a yeast cell, most preferably *Saccharomyces cerevisiae* or *Schizosaccharomyces pombe*. In one format, a first chimeric gene is provided. The first chimeric gene comprises a DNA sequence that encodes a first protein or fragment fused to a G protein gamma subunit.

A second gene is provided which is capable of being expressed in the host cell. The second gene encodes a second test protein which will typically be expressed in its native form. In one embodiment, both the first and the second genes are introduced into the host cell cloned into appropriate plasmids or expression vectors. The first chimeric gene may also be present in a chromosome of the host cell and the second gene is introduced into the host cell as part of a vector, or vice-versa. In another embodiment, the second gene may be natively expressed in the host cell.

Vectors useful for practicing the present invention include plasmids, viruses, and integratable DNA fragments (i.e., fragments integratable into the host genome by homologous or nonhomologous recombination). The vector may replicate and function independently of the host genome, as in the case of a plasmid, or may integrate into the genome itself, as in the case of an integratable DNA fragment. Suitable vectors will contain replicon and control sequences which are derived from species compatible with the intended expression host. For example, a promoter operable in a host cell is one which binds the RNA polymerase of that cell, and a ribosomal binding site operable in a host cell is one which binds the endogenous ribosomes of that cell.

Transformation or transfection of the vectors into suitable host cells may be accomplished by any means available, such as those disclosed by Ausubel et al. ((1987), Current Protocols in Molecular Biology, Wiley-Interscience, New York). Transformed host cells employed in the present invention are cells which have been transformed or transfected with the vectors constructed using recombinant DNA techniques and express the protein or protein subunit coded for by the heterologous DNA sequences. The host cells may be, but are not required to be, incapable of expressing an endogenous G protein gamma-subunit corresponding to the G protein gamma subunit to which the first protein is fused.

Although the methods of the present invention are not limited to yeast cells, a variety of yeast cultures, and suitable expression vectors for transforming yeast cells, are known. See, e.g., U.S. Pat. Nos. 4,745,057; 4,797,359; 4,615,974; 4,880,734; 4,711,844; and 4,865,989. *Saccharomyces cerevisiae* is the most commonly used among the yeast, although a number of other strains are commonly available. See, e.g., U.S. Pat. No. 4,806,472 (*Kluveromyces lactis* and expression vectors therefor); and U.S. Pat. No. 4,855,231 (*Pichia pastoris* and expression vectors therefor).

Yeast vectors may contain an origin of replication from the 2 micron yeast plasmid or an autonomously replicating sequence (ARS), a promoter, DNA encoding the heterologous DNA sequences, sequences for polyadenylation and transcription termination, and a selection gene. An exemplary plasmid is YRp7, (Stinchcomb et al., (1979) *Nature* 282:39; Kingsman et al., (1979) *Gene* 7:141; or Tschemper et al., (1980) *Gene* 10:157). This plasmid contains the TRP1 gene, which provides a selection marker for a mutant strain of yeast lacking the ability to grow in tryptophan, for example ATCC No. 44076 or PEP4-1 (Jones, (1977) *Genetics* 85, 12). The presence of the trp1 lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al., (1980) *J. Biol Chem.* 255: 2073 or other glycolytic enzymes (Hess et al., (1968) *J Adv. Enzyme Reg.* 7:149; and Holland et al., (1978) *Biochemistry* 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization.

In constructing suitable expression plasmids, the termination sequences associated with these genes may also be ligated into the expression vector 3' of the heterologous coding sequences to provide polyadenylation and termination of the mRNA.

As discussed above, induction of a G protein signaling cascade may be required to induce a detectable phenotype which is dependent upon the interaction of the first and second proteins used in the invention. The choice of inducing agent depends in part upon the choice of detectable phenotype selected as well as the effector molecule involved in the signaling pathway. For instance, in yeast wherein pheromone induced growth inhibition is used as the detectable phenotype, α-factor pheromone is employed to induce the G protein signaling cascade. Alternatively, available agonists of any G protein-coupled receptor may be used to induce a specific phenotype such as hormones, neurotransmitters and growth factors (see Muller et al. (1995) *Biochem. Soc. Trans.* 23(1):141–8 and Dohlman et al. (1997) *J Biol Chem.* 272(7):3871–3874). Exposure to differing amounts of an inducing agent may be used to modulate the detectable phenotype.

The above methods may be modified to identify agents which modulate at least one interaction between the first and second proteins. In this format, vectors encoding a first protein fused to a G protein gamma subunit and a second protein are prepared. Generally, the first and second protein will be previously identified. Further, the interaction between the first protein and the second protein will typically be associated with a given disease state, condition or clinical indication.

Cells which express a first protein fused to a G protein gamma subunit and a second protein are exposed or incubated with the agent. The cells are then assayed for the ability of the agent to modulate an interaction between the first and second protein. In this format, cells exposed to the agent which inhibits an interaction between the first and second proteins will exhibit changes in the detectable phenotype being assayed. This change in detectable phenotype occurs, after induction of a G protein signaling cascade, when the G protein subunits dissociate and G beta/gamma is free to activate a signaling pathway leading to the detectable phenotype. In control cells not exposed to the agent, the interaction of the first and second proteins prevents beta/gamma from interacting with the normal effector to activate the signaling pathway.

The above methods may be used to identify new, previously unidentified binding partners for a known protein. In one format, a known protein may be expressed in its native form as the second protein to screen for potential binding partners expressed from a library of G protein gamma subunit fusions as the first protein. In another format, the first protein may be a known protein expressed as a G protein gamma subunit fusion to screen for potential binding partners expressed as the second protein from a cDNA library.

The methods of the invention may also be modified to detect and identify mutations which modulate protein-protein interactions between two binding partners. As an example, mutations in a first protein fused to a G protein gamma subunit which affect the binding to a second protein may be assayed by preparing a library of mutations fused in frame to the G protein gamma subunit. Mutations may be produced by any means available in the art, such as site directed (oligonucleotide-directed) mutagenesis, linker insertion or scanning mutagenesis, deletion mutagenesis or mutations induced in Sec-1 by chemical mutagenesis. See Sambrook et al. for a variety of available site-directed and random mutagenesis methods.

In an alternative format, mutations in a second protein which affect the binding of the second protein to a first protein fused to a G protein gamma subunit may be assayed by preparing a library of mutations in the second protein. Mutations in the second protein may also be prepared using any available means including site directed (oligonucleotide-directed) mutagenesis, linker insertion or scanning mutagenesis, deletion mutagenesis or mutations induced by chemical mutagenesis.

The methods of the present invention, as described above, may be practiced using a kit for detecting interactions between a first test protein and a second test protein. The kit may include a container, two vectors, and a host cell. The first vector contains a promoter and may include a transcription termination signal functionally associated with the coding sequence for a G protein gamma subunit. The first vector includes a restriction site(s) for inserting a DNA sequence encoding a first test protein or protein fragment in such a manner that the first test protein is expressed as part of a fusion protein with the G protein gamma subunit. The first vector may include the coding sequence for a known protein fused in frame to the coding sequence for a G protein gamma subunit. Alternatively, the first vector may be supplied as a population of vectors comprising a library of cDNA fragments fused in frame to the coding sequence for a G protein gamma subunit.

The kit includes a second vector which includes a promoter and a transcription termination signal to direct transcription. The second vector also includes a restriction site(s) to insert a DNA sequence encoding the second test protein or protein fragment into the vector, in such a manner that the second test protein is capable of being expressed in a relevant host cell. The second vector may include the coding sequence for a known protein. Alternatively, the second vector may be supplied as a population of vectors comprising a library of cDNA fragments.

The kit may also include a host cell, preferably a yeast strain of *Saccharomyces cerevisiae* or *Schizosaccharomyces pombe*.

The following working examples specifically point out preferred embodiments of the present invention, and are not to be construed as limiting in any way the remainder of the disclosure. Other generic configurations will be apparent to one skilled in the art.

EXAMPLE 1

Production of G Protein Gamma Subunit Fusion Vectors

The production of G protein gamma fusions to a protein of interest may be accomplished using any available vectors designed to replicate and express the fusion protein in the appropriate host cell.

Figure 2A:
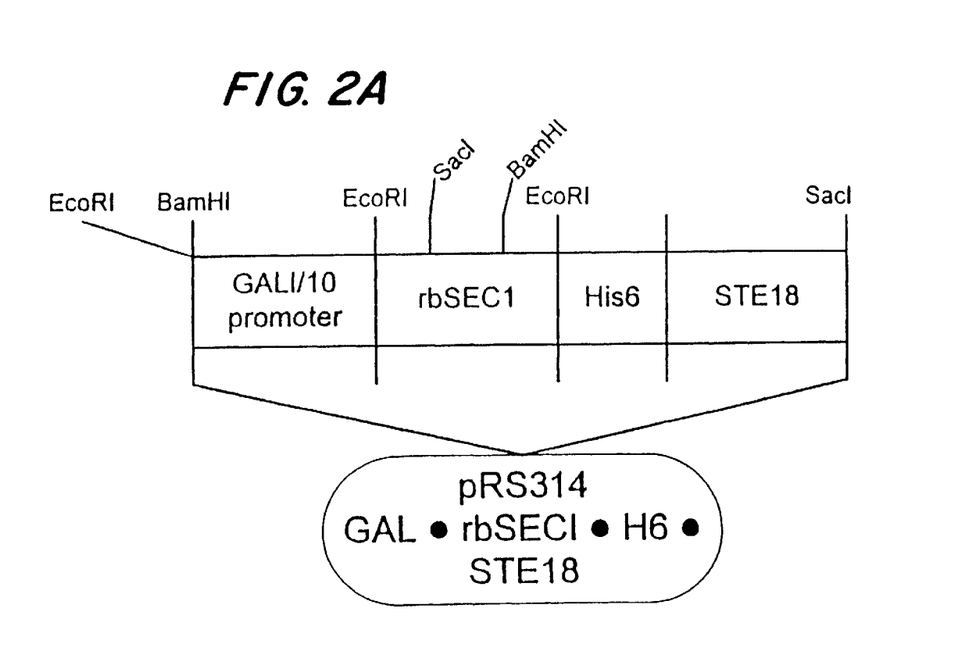
FIGS. 2A and 2B are schematics of pRS314-GAL-rbSec1-H6STE18 and pRS316-ADH-syntaxin.
Figure 2B:
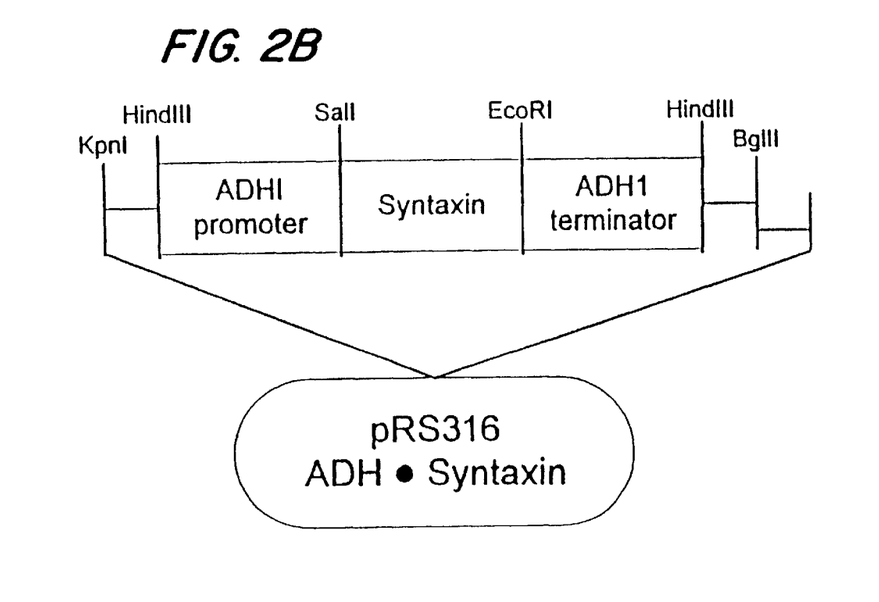

When yeast cells are used as the host cell, pRS316-GAL-STE4 was constructed by ligation of the EcoRI-SalI fragment from pL19, containing the bidirectional galactose-inducible GAL1/10 promoter and STE4 (Gβ gene) (Whiteway et al., (1990) Overexpression of the STE4 gene leads to mating response in haploid *Saccharomyces cerevisiae, Molecular and Cellular Biology* 10:217–222.) into the vector pRS316 (described by Sikorski et al., (1989) A system of shuttle vectors and yeast host strains designed for efficient manipulation of DNA in *Saccharomyces cerevisiae. Genetics* 122:19–27.). STE18 (Gγ gene) was PCR amplified using the plasmid M57p4 as the template (Whiteway et al.) and oligonucleotides that flank the STE18 open reading frame (GGG AAT TCA ATG GCT CAC CAT CAC CAT CAC CAT GCT AGC ATG ACA TCA GTT CAA AAC TCT CC, (SEQ ID NO: 1) 5' oligo, encoding 6 His residues upstream of the amino terminus; GAG GCT CTA CGT AGC AAG, (SEQ ID NO: 2) 3'oligo). The PCR product was digested with EcoRI and SacI, and ligated to the corresponding sites in pRS316-GAL-STE4 described above to produce pRS316-GAL-STE4/18-H6.

pRS314-GAL-H6-STE18 (FIG. 2) was constructed by ligation of the BamHI-SacI fragment from pRS316-GAL-STE4/18-H6 into pRS314. To prepare fusions of a protein of interest to the yeast G protein gamma subunit, the coding sequence of the protein is inserted in frame into the EcoRI site of pRS314-GAL-H6-STE18 to yield pRS314-GAL-heterologous gene-H6STE18.

EXAMPLE 2

A Method of Detecting the Interaction Between Two Proteins

Production of a Rat Sec-1- G Protein Gamma Subunit Fusion and Transformation of Host Cells Expressing the Sec-1 G Protein Gamma Subunit Fusion and Syntaxin Strains, Media and Transformation Standard methods for the growth, maintenance, and transformation of yeast and bacteria, and for the manipulation of DNA, were used throughout (Ausubel et al. 1987, Current Protocols in Molecular Biology. Wiley-Interscience, New York). The *Escherichia coli* strain DH5α was used for the maintenance of plasmids. Yeast cells were grown in synthetic medium supplemented with amino acids, adenine and 2% glucose (SCD) or 2% galactose plus 0.2% sucrose (SCG); tryptophan and/or uracil were omitted to maintain selection for plasmids. The *Saccharomyces cerevisiae* strain used in this study was MHY6 (from Jeremy Thomer) (MATa ura3-52 lys2-801$^{am}$ ade2-101$^{oc}$ trp1-Δ63 his3-Δ200 leu2-Δ1 ste18Δ::LEU2) (derived from Sikorski et al. (1989) *Genetics* 122(1):19–27).

Plasmid Construction pRS316-GAL-STE4 was constructed by ligation of the EcoRI-SalI fragment from pL19, containing the bidirectional galactose-inducible GAL1/10 promoter and STE4 (Gβ gene) (from Whiteway et al.) into the vector pRS316 (described in Sikorski et al, (1989) A system of shuttle vectors and yeast host strains designed for efficient manipulation of DNA in *Saccharomyces cerevisiae. Genetics* 122:19–27.). STE18 (Gγ gene) was PCR amplified using the plasmid M57p4 as the template (from Whiteway et al.) and oligonucleotides that flank the STE18 open reading frame (GGG AAT TCA ATG GCT CAC CAT CAC CAT CAC CAT GCT AGC ATG ACA TCA GTT CAA AAC TCT CC, (SEQ ID NO: 1) 5' oligo, encoding 6 His residues upstream of the amino terminus; GAG GCT CTA CGT AGC AAG, (SEQ ID NO: 2) 3'oligo). The PCR product was digested with EcoRI and SacI, and ligated to the corresponding sites in pRS316-GAL-STE4 described above to produce pRS316-GAL-STE4/18-H6.

pRS314-GAL4H6-STE18 was constructed by ligation of the BamHI-SacI fragment from pRS316-GAL-STE4/18-H6 into pRS314. Rat brain Sec1 (rbSec1) was PCR amplified using a plasmid that contains the rbSEC cDNA in pBluescript II SK as a template (Garcia et al., (1994) A rat brain Sec1 homologue related to Rop and UNC18 interacts with syntaxin *Proc. Nat'l Acad. Sci. U.S.A.* 91:2003–7) and oligonucleotides that flank the Sec1 open reading frame (CCG AAT TCC ATG GCC ATT GGC CTC AAG, (SEQ ID NO:3) 5' oligo, containing an EcoRI site beginning 7 nucleotides upstream of the initial ATG; CCT GAA TTC GAG CTT ATT TCT TCG TCT GTT TTA TTC AG, (SEQ ID NO: 4) 3' oligo, containing an EcoRI site in frame with the N-terminal open reading frame of His6-STE18). The rbSec1 PCR product was digested with EcoRI and ligated into the EcoRI site of pRS314-GAL-H6-STE18 to yield pRS314-GAL-rbSec1-H6STE18.

pRS316-ADH (amp$^r$, CEN/ARS, URA3 and ADH1 promoter and termination sequence) (described in Song et al., (1996) Regulation of membrane and subunit interactions by N-myristoylation of a G protein a subunit in yeast. *J. Biol. Chem.* 271:20273–20283.). Rat syntaxin 1a was PCR amplified using a cDNA in vector CDM8 as the template, (Blasi et al. (1993). Botulinum neurotoxin C1 blocks neurotransmitter release by means of cleaving HPC-1/syntaxin. *EMBO J.* 12:4821–8.) and oligonucleotides that flank the syntaxin open reading frame (CGC GGG TCG ACA TGA AGG ACC GAA CCC AGG, (SEQ ID NO:5) 5' oligo, containing a SalI site beginning 6 nucleotides upstream of the initial ATG; CCG AAT TCA CTA TCC AAA GAT GCC CCC GAT GG, (SEQ ID NO: 6) 3' oligo, containing an EcoRI site 10 nucleotides downstream of the termination codon). The PCR amplified product was digested with SalI and EcoR1 and ligated to the corresponding sites in pRS316-ADH.

Detection of Sec-1-Syntaxin Interactions
Growth Inhibition Assay

To evaluate to the interactions of the Sec-1 G protein gamma subunit fusion and syntaxin, a growth inhibition assay (halo assay) was carried out by diluting 50 μL from an overnight culture grown at 30° C. in selective media with 2 mL sterile water, followed by the addition of an equal volume of 1% (w/v) dissolved agar (55° C.) and poured onto a culture dish of SCD-Trp-Ura or SCG-Trp-Ura medium. Sterile filter discs were spotted with 5 μg or 15 μg of synthetic α-factor pheromone and placed onto the nascent lawn to induce growth arrest. The resulting zone of growth-arrested cells was documented after 2 days at 30° C.

Figure 3A:
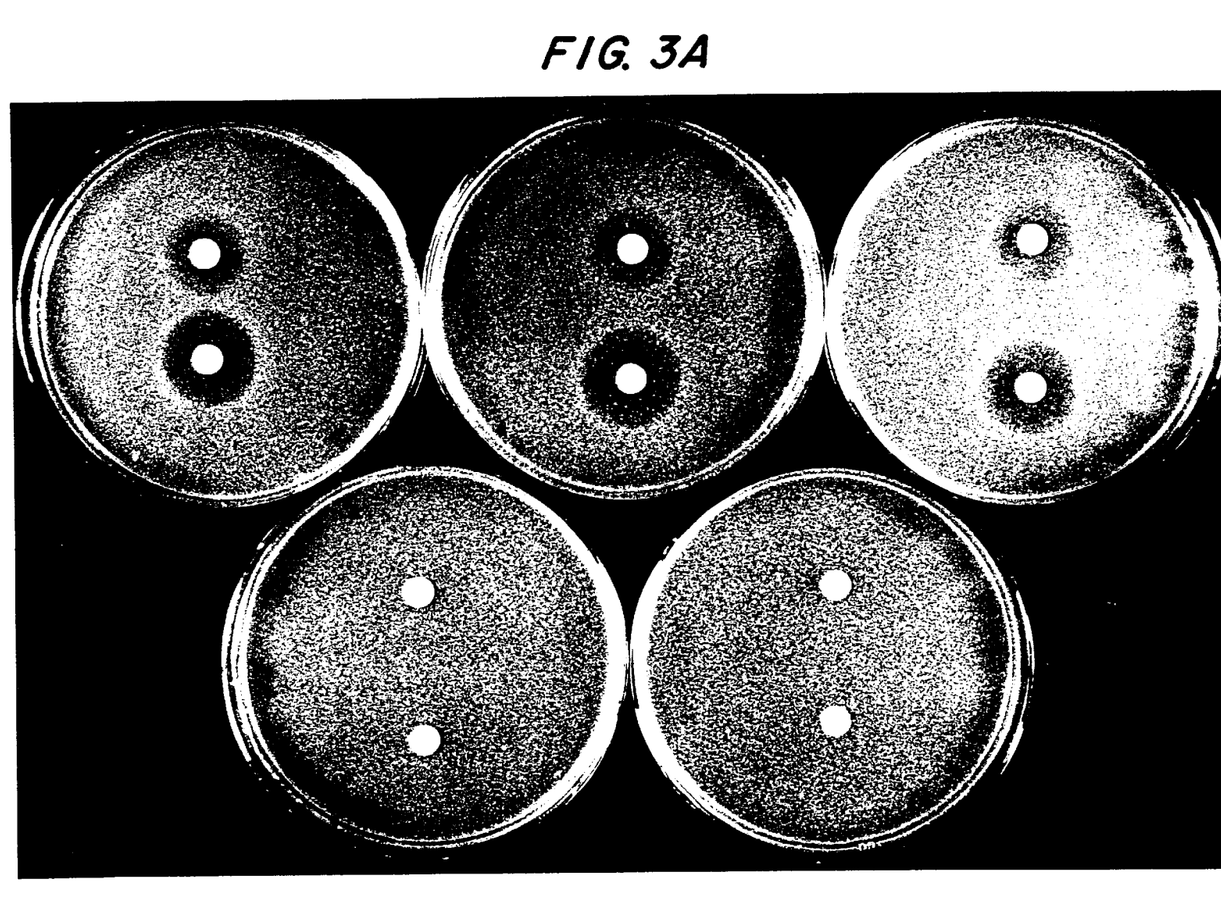
FIG. 3A represents the growth inhibition results of an assay to detect the ability of Sec-1 and syntaxin to interact and prevent pheromone induced growth inhibition.
Figure 3B:
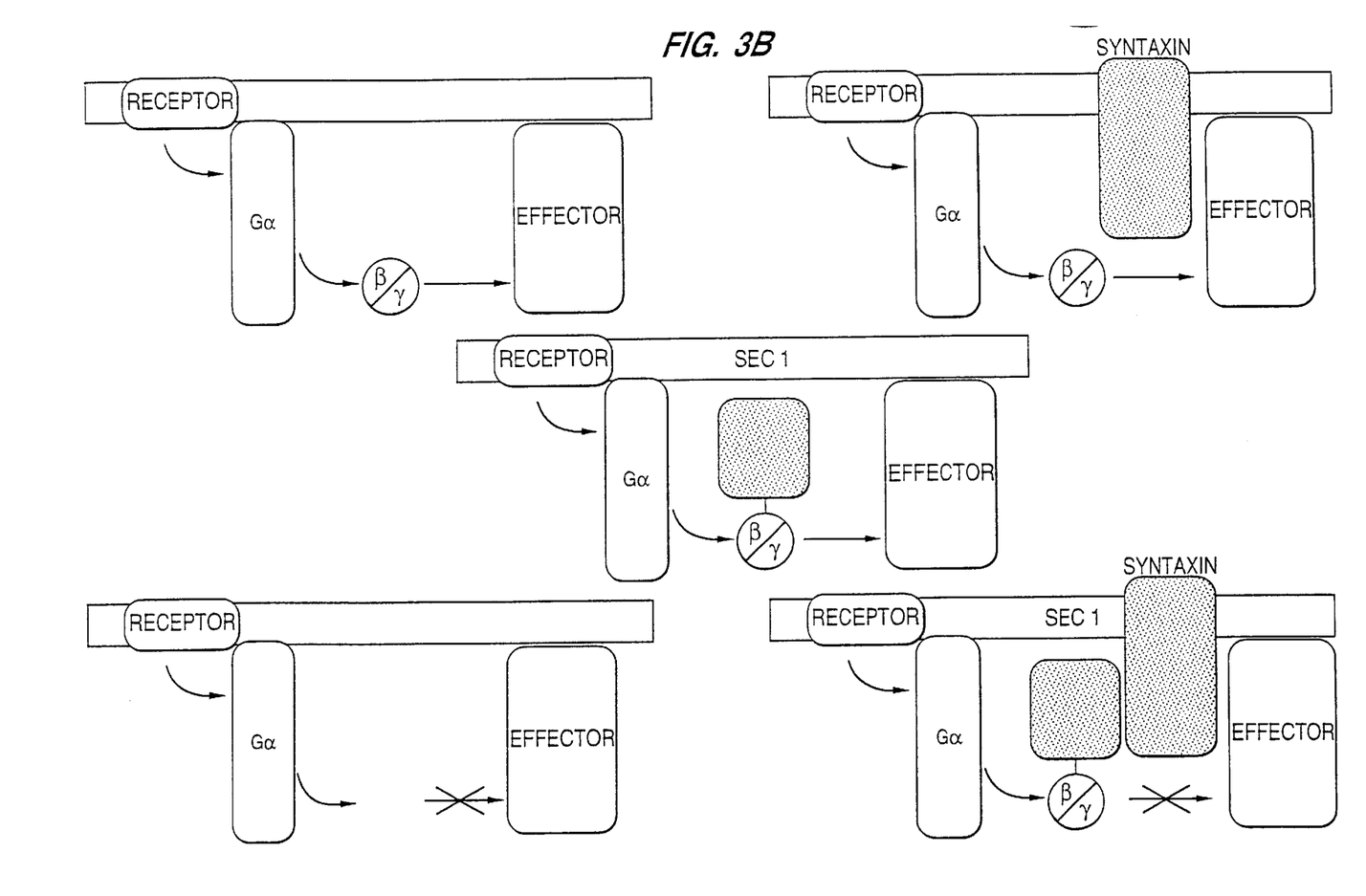
FIG. 3B is a schematic of the elements used in each growth inhibition assay.

As set forth in FIG. 3, yeast expressing the Sec-1 G protein gamma subunit fusion and syntaxin did not respond to α-factor induced growth arrest as exhibited by no zone of inhibition around filter paper disks containing 5 or 15 μg of α-factor. This is in contrast to control cells which express the Sec-1 G protein gamma fusion alone and cells which express syntaxin alone. In the control cells, upon pheromone addition, the G protein subunits dissociate and G beta/gamma is free to activate a signaling pathway leading to growth arrest. When the cells express the Sec-1 G protein gamma fusion and syntaxin, pheromone induced growth arrest is blocked because the interaction of syntaxin with Sec1 prevents the beta/gamma from interacting with the normal effector to activate the signaling pathway to growth arrest.

EXAMPLE 3
Methods for Testing the Ability of an Agent to Modulate an Interaction Between Two Proteins The system described in Example 2 may be used to screen for agents which modulate the interactions between any two proteins. As an example, agents which modulate the interactions between Sec-1 and syntaxin may be screened by exposing yeast cells expressing the Sec-1 G protein gamma fusion and syntaxin to the agent to be tested. A growth inhibition assay (halo assay) is carried out by diluting 50 μL from an overnight culture of yeast expressing the Sec-1 G protein gamma fusion and syntaxin at 30° C. in selective media with 2 mL sterile water, followed by the addition of an equal volume of 1% (w/v) dissolved agar (55° C.) and poured onto a culture dish of SCD-Trp-Ura or SCG-Trp-Ura medium with and without the agent to be tested. Sterile filter discs are spotted with 5 μg or 15 μg of synthetic α-factor pheromone and placed onto the nascent lawn to induce growth arrest. Alternatively, the agent to be tested may be spotted onto filter disks with the synthetic α-factor pheromone. The resulting zone of growth-arrested cells is then documented after 2 days at 30° C.

In control cells not exposed to the agent, pheromone induced growth arrest is blocked because the interaction of syntaxin with Sec1 prevents beta/gamma from interacting with the normal effector to activate the signaling pathway to growth arrest. In cells exposed to an agent which inhibits the interaction of Sec-1 and syntaxin, upon pheromone addition, the G protein subunits dissociate and G beta/gamma is free to activate a signaling pathway leading to growth arrest. This pheromone induced growth arrest is exhibited by a zone of inhibition around the filter disk.

In a second assay, agents which modulate the interactions between the Her-2/neu receptor tyrosine kinase which is upregulated in some cancerous cells, including some breast cancers, and Grb2 may be screened by exposing yeast cells expressing a Grb2-G protein gamma fusion and Her-2/neu to the agent to be tested. A vector comprising a Grb2-G protein gamma fusion is prepared by inserting the coding sequence for Grb2 (available in Lowenstein et al. (1992) Cell 70(3):431–442) into pRS314-GAL4-H6-STE18. A second vector encoding Her-2/neu is prepared by insertion of the coding sequence of Her-2/neu (available in Yamamoto et al (1986) *Nature* 319:230–234) into pRS316-ADH.

A growth inhibition assay (halo assay) is carried out by diluting 50 μL from an overnight culture of yeast expressing the Grb2-G protein gamma fusion and Her-2/neu at 30° C. in selective media with 2 mL sterile water, followed by the addition of an equal volume of 1% (w/v) dissolved agar (55° C.) and poured onto a culture dish of SCD-Trp-Ura or SCG-Trp-Ura medium with and without the agent to be tested. Sterile filter discs are spotted with 5 μg or 15 μg of synthetic α-factor pheromone and placed onto the nascent lawn to induce growth arrest. Alternatively, the agent to be tested may be spotted onto filter disks with the synthetic α-factor pheromone. The resulting zone of growth-arrested cells is then documented after 2 days at 30° C.

In control cells not exposed to the agent, pheromone induced growth arrest is blocked because the interaction of activated Her-2/neu with Grb2 prevents beta/gamma from interacting with the normal effector to activate the signaling pathway to growth arrest. In cells exposed to an agent which inhibits the interaction of activated Her-2/neu and Grb2, upon pheromone addition, the G protein subunits dissociate and G beta/gamma is free to activate a signaling pathway leading to growth arrest. This pheromone induced growth arrest is exhibited by a zone of inhibition around the filter disk.

EXAMPLE 4
Method for Identifying Binding Partners for a Protein

The system described in Example 2 may also be used to identify new, previously unidentified binding partners for a known protein. In one format, a known protein may be expressed in its native form, such as syntaxin, to screen for potential binding partners expressed from a library of G protein gamma subunit fusions. Syntaxin is a known target for botulinum toxin. Botulinum toxin is currently used as a therapeutic agent to treat central nervous system disorders such as spasticity among stroke patients. The identification of new binding partners for syntaxin may elucidate alternate potential drug targets for the treatment of such disorders.

Rat syntaxin 1a is PCR amplified using a cDNA in vector CDM8 as the template, (Blasi, J., E. R. Chapman, S. Yamasaki, T. Binz, H. Niemann, and R. Jahn, 1993. Botulinum neurotoxin C1 blocks neurotransmitter release by means of cleaving HPC1/syntaxin EMBO Journal 12:4821–8) and oligonucleotides that flank the syntaxin open reading frame (CGC GGG TCG ACA TGA AGG ACC GAA CCC AGG, (SEQ ID NO: 5) 5' oligo, containing a SalI site beginning 6 nucleotides upstream of the initial ATG; CCG AAT TCA CTA TCC AAA GAT GCC CCC GAT GG, (SEQ ID NO: 6) 3' oligo, containing an EcoRI site 10 nucleotides downstream of the termination codon). The PCR amplified product was digested with SalI and EcoRI and ligated to the corresponding sites in pRS316-ADH to facilitate expression of rat syntaxin 1a in a recombinant yeast cell.

First Protein Library Fusions to G Protein Gamma Subunit

A library of G Protein gamma subunit fusions is prepared by ligating a cDNA library of choice into the EcoRI site of pRS314-GAL-H6-STE18 as described above. Alternatively, appropriate vector backbones may be substituted depending on the cell in which the G protein gamma subunit fusions are to be expressed.

To prepare the library of G protein gamma subunit fusions, the cDNA inserts from a rat brain cDNA library purchased from Stratagene (Cat. No. 936501) are released from the backbone vector using standard procedures and inserted into the EcoRI site of pRS314-GAL-H6-STE18. This library is then transformed into yeast which express rat syntaxin 1a and a lacZ reporter gene fused downstream from the FUS1 pheromone inducible promoter (Nomoto et al. (1990) EMBO J. 9:691) by the methods of Ausubel et al.

Screening and identification for proteins which interact with syntaxin are accomplished by assaying for the ability of individual fusion proteins from the G protein gamma subunit fusion library to interact with syntaxin after pheromone induction. In cells which express a G protein gamma subunit fusion which does not interact with syntaxin, upon pheromone exposure, the G protein subunits dissociate and G beta/gamma is free to activate a signaling pathway leading to transcription of the lacZ reporter gene fused downstream from the FUS1 promoter. In cells which express a G protein gamma fusion which interacts with syntaxin, pheromone induced transcription from the lacZ reporter gene fused downstream from the FUS1 promoter is blocked. In this case, the interaction of the G protein gamma subunit fusion with syntaxin prevents beta-gamma from activating a signaling pathway leading to transcription of the lacZ reporter gene fused downstream from the FUS1 promoter Individual G protein gamma subunit fusions which may interact with syntaxin are isolated by recovery and sequencing of the cDNA insert fused to the coding sequence for the G protein gamma subunit by standard cloning and sequencing techniques. Such techniques are widely available such as those disclosed by Sambrook et al. (Molecular Cloning: A Laboratory Manual, 2nd edition, Cold Spring Harbor Laboratory Press, Plainview N.Y., 1989).

Expression of cDNA Libraries as the Second Protein

In an alternative format, the rat brain library may be screened for proteins which interact with the Sec-1/G protein gamma subunit fusion expressed by pRS314-GAL-rbSec1-H6-STE18. In this format, the rat brain library cDNA described above is released from the backbone vector using standard procedures and inserted into pRS316-ADH. This library is then co-transformed into cells which contain a lacZ reporter gene fused downstream from the FUS1 pheromone inducible promoter (Nomoto et al. (1990) EMBO J. 9:691) with pRS314-GAL-rbSec1-H6-STE18.

Proteins which interact with Sec-1 are identified by assaying for the ability of individual proteins encoded by the library to interact with Sec-1 after pheromone induction. In cells which express a protein encoded by a member of the rat cDNA library which does not interact with the Sec-1/G protein gamma subunit fusion, upon pheromone exposure, the G protein subunits dissociate and G beta-gamma is free to activate a signaling pathway leading to transcription of the lacZ reporter gene fused downstream from the FUS1 promoter. In cells which express a library protein which does interact with the Sec-1/G protein gamma fusion, pheromone induced transcription from the lacZ reporter gene fused downstream from the FUS1 pheromone inducible promoter is blocked. In this case, the interaction of the Sec-1/G protein gamma subunit fusion with the library protein prevents the beta/gamma from activating a signaling pathway leading to transcription of the lacZ reporter gene fused downstream from the FUS1 promoter.

Individual cDNAs encoding library proteins which may interact with Sec-1 are isolated by recovery and sequencing of the cDNA insert by standard cloning and sequencing techniques. Such techniques are widely available such as those disclosed by Sambrook et al. (Molecular Cloning: A Laboratory Manual, 2nd edition, Cold SPRING Harbor Laboratory Press, Plainview N.Y., 1989).

EXAMPLE 5

Method for Identifying Mutations Which Disrupt Protein-Protein Interactions

The system described in Example 2 may also be used to screen for the effects of mutations which modulate protein-protein interactions between two binding partners. As an example, mutations in Sec-1 which effect the binding of Sec-1 to syntaxin may be assayed by preparing a library of Sec-1 mutations fused in frame to the G protein gamma subunit as described above. Mutations in Sec-1 may be produced by any means available in the art, such as site directed (oligonucleotide-directed) mutagenesis, linker insertion or scanning mutagenesis, deletion mutagenesis or mutations induced in Sec-1 by chemical mutagenesis. See Sambrook et al. for a variety of available site-directed and random mutagenesis methods.

Mutations in Sec-1 are then screened for their ability to disrupt Sec-1 binding to syntaxin by transforming cells which express syntaxin from pRS316-ADH-syntaxin with pRS314GAL-rbSec1(mut)-H6STE18 (rbSec-1(mut) encoding a Sec-1 mutation). Growth inhibition assays (halo assays) are carried out by diluting 50 µL from an overnight culture grown at 30° C. in selective media with 2 mL sterile water, followed by the addition of an equal volume of 1% (w/v) dissolved agar (55° C.) and poured onto a culture dish of SCD-Trp-Ura or SCG-Trp-Ura medium. Sterile filter discs are spotted with 5 µg or 15 µg of synthetic α-factor pheromone and placed onto the nascent lawn to induce growth arrest. The resulting zone of growth-arrested cells is documented after 2 days at 30° C.

Yeast expressing wild-type (non-mutated) Sec-1 G protein gamma subunit fusion and syntaxin do not respond to α-factor induced growth arrest as exhibited by no zone of inhibition around filter paper disks containing 5 or 15 µg of α-factor. This is contrast to cells which express Sec-1 G protein gamma fusions wherein Sec-1 contains a mutation that disrupts Sec-1-syntaxin binding. In these cells, upon pheromone addition, the G protein subunits dissociate and G beta/gamma is free to activate a signaling pathway leading to growth arrest.

In an alternative format, mutations in syntaxin which affect the binding of syntaxin to Sec-1 may be assayed by preparing a library of syntaxin mutations as described above. Mutations in syntaxin may be prepared by any available means including site directed (oligonucleotide-directed) mutagenesis, linker insertion or scanning mutagenesis, deletion mutagenesis or mutations induced in syntaxin by chemical mutagenesis.

Mutations in syntaxin are then screened for their ability to disrupt syntaxin binding to Sec-1 by transforming cells which express a Sec-1/G protein gamma subunit fusion, such as that encoded by pRS314-GAL-rbSec1-H6-STE18 with pRS316 ADH-syntaxin* (wherein "syntaxin*" refers to a syntaxin mutation). Growth inhibition assays (halo assays) are carried out by diluting 50 μL from an overnight culture grown at 30° C. in selective media with 2 mL sterile water, followed by the addition of an equal volume of 1% (w/v) dissolved agar (55° C.) and poured onto a culture dish of SCD-Trp-Ura or SCG-Trp-Ura medium. Sterile filter discs are spotted with 5 μg or 15 μg of synthetic α-factor pheromone and placed onto the nascent lawn to induce growth arrest. The resulting zone of growth-arrested cells is documented after 2 days at 30° C.

Yeast expressing the Sec-1 G protein gamma subunit fusion and wild-type (non-mutated) syntaxin do not respond to α-factor induced growth arrest as exhibited by the absence of a zone of inhibition around filter paper disks containing 5 or 15 μg of α-factor. This is contrast to cells which express the Sec-1 G protein gamma subunit fusion and syntaxin which contains a mutation that disrupts syntaxin-Sec-1 binding. In these cells, upon pheromone addition, the G protein subunits dissociate and G beta/gamma is free to activate a signaling pathway leading to growth arrest.

It should be understood that the foregoing discussion and examples merely present a detailed description of certain preferred embodiments. It therefore should be apparent to those of ordinary skill in the art that various modifications and equivalents can be made without departing from the spirit and scope of the invention. Once such variation includes the use of other signaling cascades which transmit signal through membrane proteins into the cell. All references, articles and patents identified above are herein incorporated by reference in their entirety.

What is claimed is:

1. A method of identifying an agent that modulates at least one interaction between two proteins comprising:
    (a) exposing a cell to the agent, the cell comprising:
        (i) a first protein, which is not a heterotrimeric G protein or subunit thereof, fused to a G protein gamma subunit; and
        (ii) a second protein, and
    (b) determining whether the interaction of the G protein gamma subunit with an effector molecule has been modulated, thereby identifying an agent that modulates at least one interaction between the two proteins.

2. The method of claim 1 wherein the cells are provided in an aqueous solution and the exposure is carried out by adding the agent to the aqueous solution.

3. The method of claim 1 wherein the cell does not express an endogenous G protein gamma subunit which interacts with the effector molecule.

4. The method of claim 1 wherein the cell expresses an active endogenous effector molecule.

5. The method of claim 1 wherein the second protein is a membrane protein.

6. The method of claim 1 wherein the agent interacts with an extracellular domain of the second protein.

7. The method of claim 1 wherein the first protein is Sec-1 and and the second protein is Syntaxin 1a.

8. The method of claim 1 wherein the first protein is Grb-2 and and the second protein is Her-2/neu.

9. The method of claim 1 wherein the effector molecule is selected from the group consisting of kinases, arresting, nucleotide cyclases, phosphodiesterases, phospolipases, small molecule transporters and channels.

10. The method of claim 1 wherein the second protein is expressed in its native form.

11. The method of claim 1 wherein the agent inhibits an interaction between the first protein and the second protein.

12. The method of claim 11 wherein the interaction of the G protein gamma subunit with the effector molecule is enhanced upon addition of the agent.

13. The method of claim 1 wherein the agent promotes an interaction between the first and second proteins.

14. The method of claim 13 wherein the G protein gamma subunit is sequestered from the effector molecule upon addition of the agent.

15. The method of claim 1 wherein the interaction of the G protein gamma subunit with an effector molecule confers a detectable phenotype upon the host cell.

* * * * *

UNITED STATES PATENT AND TRADEMARK OFFICE
CERTIFICATE OF CORRECTION

PATENT NO. : 6,482,603 B1
APPLICATION NO. : 09/709626
DATED : November 19, 2002
INVENTOR(S) : Henrik G. Duhlman and Kathleen N. Ehrhard It is certified that error appears in the above-identified patent and that said Letters Patent is hereby corrected as shown below:

In the Specifications:

Column 1, lines 15-16, delete the text "The present invention arose in part from research funded by the following federal grant monies: GM 553160." and insert the following text:

--This invention was made with government support under GM553160 awarded by National Institute of Health. The government has certain rights in the invention.--

Signed and Sealed this
Eighteenth Day of June, 2013

Teresa Stanek Rea
*Acting Director of the United States Patent and Trademark Office*